(12) United States Patent
Soma et al.

(10) Patent No.: US 6,495,678 B1
(45) Date of Patent: Dec. 17, 2002

(54) IMMUNOSUPPRESSANT CONTAINING GLUCOPYRANOSE DERIVATIVE AS ACTIVE INGREDIENT

(75) Inventors: Gen-ichiro Soma, Tokyo (JP); Nagashige Omawari, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/674,808

(22) PCT Filed: May 6, 1999

(86) PCT No.: PCT/JP99/02362
§ 371 (c)(1),
(2), (4) Date: Nov. 6, 2000

(87) PCT Pub. No.: WO99/56744
PCT Pub. Date: Nov. 11, 1999

(30) Foreign Application Priority Data

May 6, 1998 (JP) ............................................. 10-137402

(51) Int. Cl.$^7$ .......................... A61K 31/70; A61K 35/56
(52) U.S. Cl. ...................... 536/54; 536/4.1; 536/118; 536/122; 536/17.2; 514/62; 514/885; 514/547; 514/25
(58) Field of Search .......................... 536/4.1, 118, 122, 536/54, 17.2; 514/62, 885, 547, 25

(56) References Cited

U.S. PATENT DOCUMENTS 4,925,929 A * 5/1990 Toda et al. .................. 536/4.1
5,158,941 A * 10/1992 Jadhav et al. ................. 514/62
5,294,723 A * 3/1994 Imaki et al. ................. 549/417

FOREIGN PATENT DOCUMENTS

| EP | 0 444 208 A1 | 9/1991 | | |
|---|---|---|---|---|
| EP | 0 553 786 A2 | 8/1993 | | |
| JP | 63-179885 | 7/1988 | | |
| JP | 64-52793 | 2/1989 | | |
| WO | WO 97/18222 | * | 5/1997 | |
| WO | 99/18975 | | 4/1999 | .......... A61K/31/70 |

OTHER PUBLICATIONS

Patent Abstracts of Japan—11106394 (Apr. 20, 1999).
Patent Abstracts of Japan—09157284 (Jun. 17, 1997).
European Search Report dated Dec. 13, 2001.

* cited by examiner

Primary Examiner—Samuel Barts
Assistant Examiner—Devesh Khare
(74) Attorney, Agent, or Firm—Sughrue Mion, PLLC

(57) ABSTRACT

An immunosuppressant comprising Glucopyranose derivatives of the formula (I):

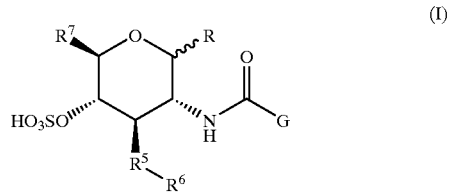

wherein R is H, OH etc; G is —$CH_2CH(R^1$—$R^2)(R^3$—$R^4)$, in which $R^1$ is a single bond, OCO-alkyl; $R^2$, $R^4$ is H, phenyl which may be substituted by halogen atoms etc.; $R^3$ is alkylene; $R^5$ is OCO-alkyl, $R^6$ is H, phenyl which may be substituted by halogen atoms etc. or $R^5$—$R^6$ is OCO—Z-(dialkoxyphenyl); $R^7$ is H, $CH_2OH$ etc; or non-toxic salts thereof as active ingredient.

Glucopyranose derivatives of the formula (I) or non-toxic salts thereof possess an activity of immunosuppression, and being useful as the prevention and/or treatment of diseases caused by abnormal enhancement of immunity, e.g. allergic diseases, autoimmune diseases.

10 Claims, No Drawings

IMMUNOSUPPRESSANT CONTAINING GLUCOPYRANOSE DERIVATIVE AS ACTIVE INGREDIENT

FIELD OF INVENTION

This invention relates to an immunosuppressant comprising Glucopyranose derivatives of the formula (I):

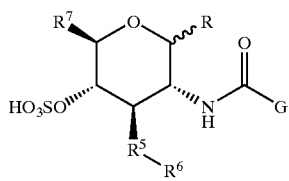

wherein all symbols are as hereinafter defined, or non-toxic salts thereof as active ingredient.

BACKGROUND

An immunoreaction is a system to protect the organism from a foreign matter as a protective reaction. However, sometimes an injury is happened for an organism by an immunoreaction that naturally plays to protect an organism. As diseases caused by the above injury, there are allergic diseases and autoimmune disease.

Recently, allergic diseases, e.g. allergic asthma, atopic dermatitis containing urticaria, allergic rhinitis, allergic conjunctivitis, allergic bronchopulmonary aspergillosis, allergic eosinophilic gastroenteritis, are increased. It is consider that these diseases are caused by peculiarity IgE antibody against an antigen in blood. Then there is lot of case that interleukin 5 (IL-5) and eosinophils are increased in a chronic condition. And the increase is also showed in a mild case. Allergic bronchopulmonary aspergillosis is asthma as a spore of aspergillosis is an antigen, and it possesses a peculiarity IgE antibody. And it showed an acute cutireaction. The treatment is same method with generally bronchial asthma [Saishin Naikagaku Taikei 61 (Nakayama): pneumonia·interstitial pneumonia, 157–158 (1992); Saishin Naikagaku Taikei 62 (Nakayama): bronchial asthma·allergic asthma, 81–91 (1992)].

One of the allergic diseases excepted the above, with the proviso that a part is overlapped, is hyper IgE syndrome containing purulence, low of wandering of leukocyte and atopic dermatitis. It is showed an abnormal mechanism of neutrophil. It is characteristic to show hyper IgE in blood, an atopic dermatitis like eczema and an infection by recurrent yellow staphylococcosis [Tadamichi MASU et al., hyper IgE syndrome, new allergic dermatitis (editor is Hikotaro Yoshida), 143 (1991)].

Besides, PIE syndrome, pulmonary eosinophilia, e.g. Loeffler syndrome, chronic eosinophilic pneumonia, acute eosinophilic pneumonia, tropical eosinophilia, allergic granulomatous angiitis, allergic bronchopulmonary mycosis, eosinophilia; and eosinophilic fasciitis accompanying increases of IL-5 and IgE antibody in a serum are known as allergic diseases [Enright T. et al., "Pulmonary eosinophilic syndrome" Ann. Allergy, 62, 277 (1989), and Saishin naikagaku taikei 24 (Nakayama): collagen diseases, similarity diseases thereof, 112–116 (1992)].

Allergic diseases that caused by abnormal enhancement of immunity, such as an increase of IgE antibody that is peculiarity against an antigen, increases of IL-5 and eosinophils, are increased.

General treatments of allergic diseases are carried out to prevent an inhalation or take of antigen, e.g. cedar pollens, acarid, spore of aspergillosis and some foods; into body, and to use medicines, e.g. anti-histamine, steroid.

However, a fundamentally treatment is difficult. As mentioned above, if abnormal enhancement of immunity, e.g. increases of IgE antibody that is peculiarity against an antigen, IL-5 and eosinophils, are main reasons of allergic diseases, use of medicines possessed an inhibitory activity of enhancement of immunity has a possibility to be a fundamentally treatment of allergic diseases.

On the other hand, T cells also play an important roll on an immunoreaction. An activated T cells product various cytokines, such as interleukin 4 (IL-4), interleukin 2 (IL-2), interferon $\gamma$ (IFN-$\gamma$), and assist an activity of immunoreaction.

The other way, a production of these cytokines also causes allergic diseases and autoimmune disease. IL-4 is related mainly to an activity of B cells stimulated by antigen, and it promotes a production of IgE. IL-2 has an increasing activity for T cells and B cells stimulated by antigen. IFN-$\gamma$ causes an inducement of differentiates of killer T cells and an activity of macrophage.

Accordingly, it is expected to improve allergic diseases, such as diseases described hereinbefore and autoimmune disease, e.g. chronic rheumatism, psoriasis, multiple sclerosis, and ulcerative colitis, which related to immunoreaction.

Glucopyranose derivatives of the present invention of the formula (I)

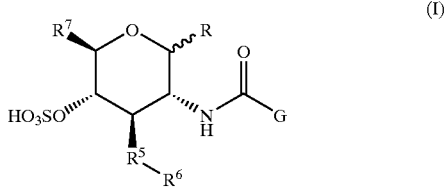

wherein all symbols are as hereinafter defined; or non-toxic salts thereof are disclosed to have an activity of lipid A like, and an activation of immune, e.g. activation of macrophage, a blastogenesis action of B cells, an product action of non-peculiar antibody, an activation of cell-mediated immunity; antineoplastic activity, e.g. an activation of inducement of interferon, an activation of product of interleukin, an activation of inducement of TNF; in Japanese Kokoku-koho Hei 4-74359 (EP 0226381) or Japanese Kokai-koho Hei 1-52793 (EP 0288888).

Besides, in the compound of the formula (I), various non-toxic salts of 2-deoxy-2-[3S-(9-phenylnonanoyloxy) tetradecanoyl]amino-3-O-(9-phenylnonanoyl)-4-O-sulfo-D-glucopyranose of the formula (I-A)

(I-A)

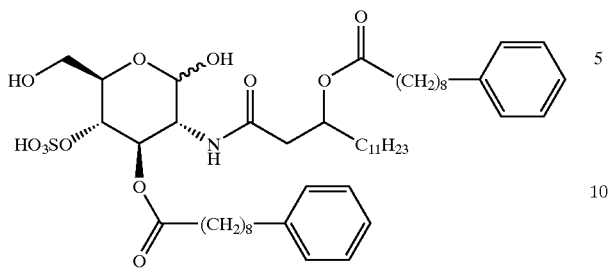

are disclosed in Japanese Kokai-koho Hei 6-41175 (EP 0226381).

However, there is no report that Glucopyranose derivatives of the present invention of the formula (I) or non-toxic salts thereof possess an activity of immunosuppression.

DISCLOSURE OF THE INVENTION

Energetic investigations have been carried out in order to make a compound having an activity of immunosuppression, e.g. IgE antibody production inhibition, and a high safety. The present inventors have found that Glucopyranose derivatives of the formula (I) or non-toxic salts thereof accomplished the present purpose.

The present invention relates to an immunosuppressant comprising Glucopyranose derivatives of the formula (I):

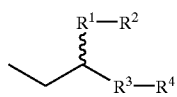

(I)

wherein R is hydrogen, hydroxy or C1–4 alkoxy,

G is (1)

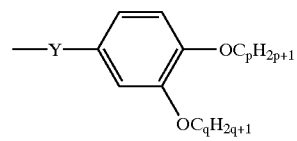

in which $R^1$ is a single bond or C2–20 oxycarbonylalkyl, $R^2$ is hydrogen or

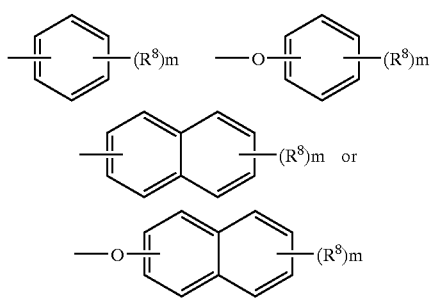

in which $R^8$ is hydrogen, C1–7 alkyl, C1–7 alkoxy or halogen atoms, m is 1, 2 or 3;

$R^3$ is C1–20 alkylene, $R^4$ is hydrogen or

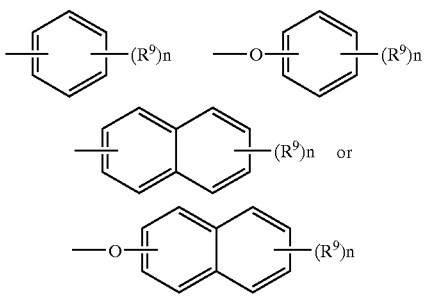

in which $R^9$ is hydrogen, C1–7 alkyl, C1–7 alkoxy or halogen atoms, n is 1, 2 or 3; or (2)

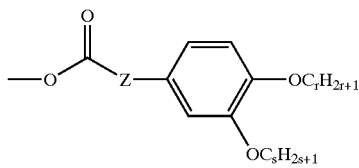

in which Y is a single bond or C1–4 alkylene, p and q independently, is an integral of 6–12;

$R^5$ is C2–20 oxycarbonylalkyl, $R^6$ is hydrogen or

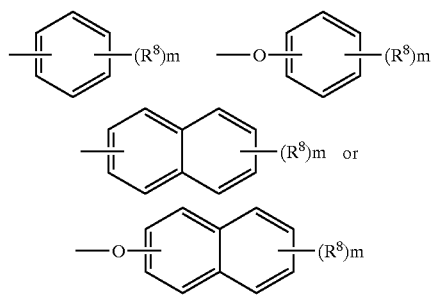

in which $R^8$ and m are as hereinbefore defined; or $R^5$–$R^6$ is

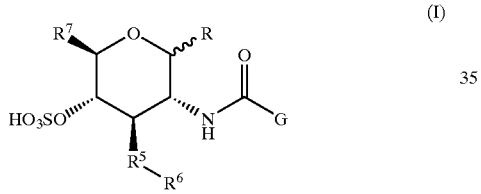

in which Z is a single bond or C1–4 alkylene, r and s, independently, is an integral of 6–12;

$R^7$ is hydrogen, methyl, hydroxymethyl or sulfoxymethyl;

with the proviso that (1) $R^2$, $R^4$ and $R^6$ is not hydrogen at the same time, (2) when $R^1$ is C2–20 oxycarbonylalkyl, then $R^2$ bonds to alkyl in $R^1$, (3) when $R^5$ is C2–20 oxycarbonylalkyl, then $R^6$ bonds to alkyl in $R^5$;

or non-toxic salts thereof as active ingredient.

DETAIL OF THE PRESENT INVENTION

In the formula (I), C1–4 alkoxy represented by R means methoxy, ethoxy, propoxy, butoxy and isomeric groups thereof. Preferable R is hydrogen, hydroxy, methoxy, and more preferable group is hydrogen, hydroxy.

In the formula (I), C2–20 oxycarbonylalkyl represented by $R^1$ in G and $R^5$ means

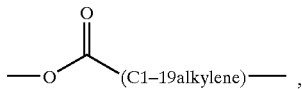

and $R^2$ or $R^6$ bond to the above alkylene. C1–19 alkylene means methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene and isomeric groups thereof.

Preferable $R^1$ is a single bond, at that time preferable $R^2$ is hydrogen; oxycarbonylhexamethyl, oxycarbonylheptamethyl, oxycarbonyloctamethyl, oxycarbonylnonamethyl and oxycarbonyloctamethyl and more preferable group is a single bond, at that time preferable $R^2$ is hydrogen, and oxycarbonyloctamethyl.

Preferable C2–20 oxycalbonylalkyl represented by $R^5$ is oxycarbonylhexamethyl, oxycarbonylheptamethyl, oxycarbonyloctamethyl, oxycarbonylnonamethyl and oxycarbonyldecamethyl, and more preferable group is oxycarbonyloctamethyl.

In the formula (I), C1–7 alkyl represented by $R^2$ in G, $R^8$ in $R^6$, and $R^9$ in $R^4$ of G means methyl, ethyl, propyl, butyl, pentyl, hexyl, heptyl and isomeric groups thereof.

In the formula (I), C1–7 alkoxy represented by $R^8$ and $R^9$ means methoxy, ethoxy, propoxy, butoxy, pentyloxy, hexyloxy, heptyloxy and isomeric groups thereof.

In the formula (I), halogen atoms represented by $R^8$ and $R^9$ means chloride, bromide, fluoride, and iodide.

Preferable $R^8$ and $R^9$ is hydrogen, halogen atoms, and more preferable group is hydrogen and chloride.

In the formula (I), C1–20 alkylene represented by $R^3$ means methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene icosamethylene and isomeric groups thereof.

Preferable $R^3$ is nonamethylene, decamethylene, undecamethylene, dodecamethylene, tridecamethylene, and more preferable group is undecamethylene.

In the formula (I), C1–4 alkylene represented by Y in G and Z in $R^5$–$R^6$ means methylene, ethylene, trimethylene, tetramethylene and isomeric groups thereof.

Preferable Y and Z are a single bond.

In the formula (I), preferable p and q in G, and r and s in $R^5$–$R^6$ is 9, 10 and 11, and more preferably is 10.

In the formula (I), preferable $R^7$ is hydrogen and hydroxymethyl.

Unless otherwise specified, all isomers are included in the present invention. For example, alkyl, alkoxy and alkylene include straight and branched isomers. Isomers resulting from the presence of asymmetric carbon(s) are also included within the present invention. Straight isomer is preferable.

In the compounds of the present invention of formulae (I), the following example compounds, the compounds described in examples of Japanese Kokoku-koho Hei 4-74359 (EP 0226381), Japanese Kokai-koho Hei 1-52793 (EP 0288888), and the compounds in the following Table 1–8 and the salts thereof are preferred.

In the Table 1–8, OMe is methoxy, Ph is phenyl, Me is methyl, OBu is butoxy. A front figure of the group means a position of substitution thereof. Di and tri means two substitutions and three substitutions. Various alkoxy and alkyl are straight alkoxy and alkyl.

For example, in each Table 1–4, 867 compound are included. It is a combination of three groups of (1)–(3) as R, and 17 groups of (1)–(17) as

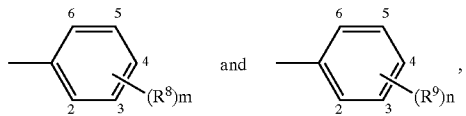

that is 3×17×17=867.

In the same way, in each Table 5–8, 168 compounds are included. It is a combination of three groups of (1)–(3) as R, 8 groups of (1)–(8) as G, and 7 groups of (1)–(7) as

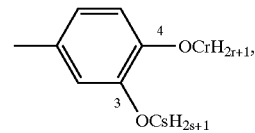

that is 3×7×8=168.

TABLE 1

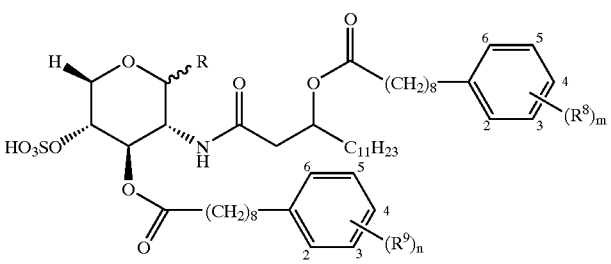
(I-1)

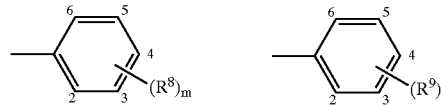

| R | | |
|---|---|---|
| (1) H | (1) Ph | (1) Ph |
| (2) OH | (2) 2-Cl—Ph | (2) 2-Cl—Ph |
| (3) OMe | (3) 2-Me—Ph | (3) 2-Me—Ph |
| | (4) 2-OBu—Ph | (4) 2-OBu—Ph |
| | (5) 3-Cl—Ph | (5) 3-Cl—Ph |
| | (6) 3-Me—Ph | (6) 3-Me—Ph |
| | (7) 3-OBu—Ph | (7) 3-OBu—Ph |
| | (8) 4-Cl—Ph | (8) 4-Cl—Ph |
| | (9) 4-Me—Ph | (9) 4-Me—Ph |
| | (10) 4-OBu—Ph | (10) 4-OBu—Ph |
| | (11) 2,4-diCl—Ph | (11) 2,4-diCl—Ph |
| | (12) 3,4-diCl—Ph | (12) 3,4-diCl—Ph |
| | (13) 2,4,6-triCl—Ph | (13) 2,4,6-triCl—Ph |
| | (14) 2,4-diOBu—Ph | (14) 2,4-diOBu—Ph |
| | (15) 3,4-diOBu—Ph | (15) 3,4-diOBu—Ph |
| | (16) 3-Me-4-Cl—Ph | (16) 3-Me-4-Cl—Ph |
| | (17) 3-Cl-5-OBu—Ph | (17) 3-Cl-5-OBu—Ph |

TABLE 2

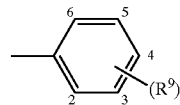
(I-2)

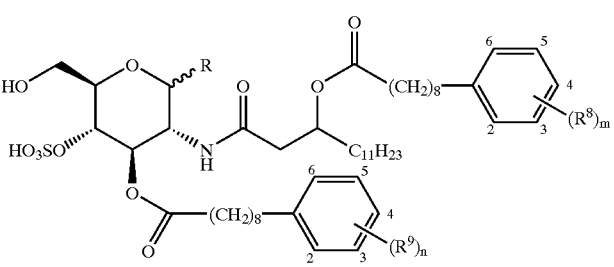

| R | | |
|---|---|---|
| (1) H | (1) Ph | (1) Ph |
| (2) OH | (2) 2-Cl—Ph | (2) 2-Cl—Ph |
| (3) OMe | (3) 2-Me—Ph | (3) 2-Me—Ph |
| | (4) 2-OBu—Ph | (4) 2-OBu—Ph |
| | (5) 3-Cl—Ph | (5) 3-Cl—Ph |
| | (6) 3-Me—Ph | (6) 3-Me—Ph |
| | (7) 3-OBu—Ph | (7) 3-OBu—Ph |
| | (8) 4-Cl—Ph | (8) 4-Cl—Ph |
| | (9) 4-Me—Ph | (9) 4-Me—Ph |
| | (10) 4-OBu—Ph | (10) 4-OBu—Ph |
| | (11) 2,4-diCl—Ph | (11) 2,4-diCl—Ph |
| | (12) 3,4-diCl—Ph | (12) 3,4-diCl—Ph |
| | (13) 2,4,6-triCl—Ph | (13) 2,4,6-triCl—Ph |
| | (14) 2,4-diOBu—Ph | (14) 2,4-diOBu—Ph |

TABLE 2-continued
(I-2)
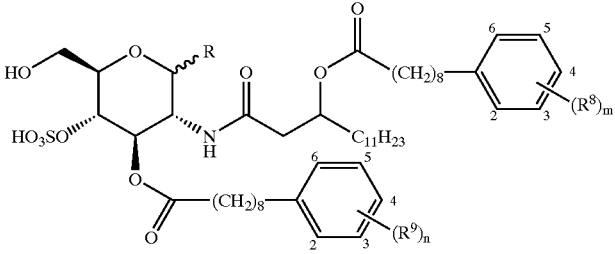
| R | (R⁸)ₘ aryl | (R⁹)ₙ aryl |
|---|---|---|
| | (15) 3,4-diOBu—Ph | (15) 3,4-diOBu—Ph |
| | (16) 3-Me-4-Cl—Ph | (16) 3-Me-4-Cl—Ph |
| | (17) 3-Cl-5-OBu—Ph | (17) 3-Cl-5-OBu—Ph |
TABLE 3
(I-3)
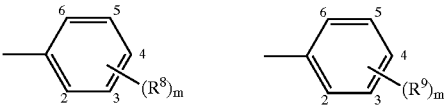
| R | (R⁸)ₘ aryl | (R⁹)ₙ aryl |
|---|---|---|
| (1) H | (1) Ph | (1) Ph |
| (2) OH | (2) 2-Cl—Ph | (2) 2-Cl—Ph |
| (3) OMe | (3) 2-Me—Ph | (3) 2-Me—Ph |
| | (4) 2-OBu—Ph | (4) 2-OBu—Ph |
| | (5) 3-Cl—Ph | (5) 3-Cl—Ph |
| | (6) 3-Me—Ph | (6) 3-Me—Ph |
| | (7) 3-OBu—Ph | (7) 3-OBu—Ph |
| | (8) 4-Cl—Ph | (8) 4-Cl—Ph |
| | (9) 4-Me—Ph | (9) 4-Me—Ph |
| | (10) 4-OBu—Ph | (10) 4-OBu—Ph |
| | (11) 2,4-diCl—Ph | (11) 2,4-diCl—Ph |
| | (12) 3,4-diCl—Ph | (12) 3,4-diCl—Ph |
| | (13) 2,4,6-triCl—Ph | (13) 2,4,6-triCl—Ph |
| | (14) 2,4-diOBu—Ph | (14) 2,4-diOBu—Ph |
| | (15) 3,4-diOBu—Ph | (15) 3,4-diOBu—Ph |
| | (16) 3-Me-4-Cl—Ph | (16) 3-Me-4-Cl—Ph |
| | (17) 3-Cl-5-OBu—Ph | (17) 3-Cl-5-OBu—Ph |

TABLE 4

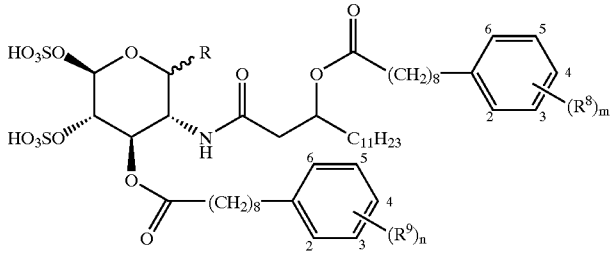
(I-4)

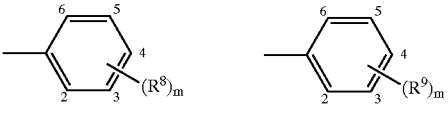

| R | $(R^8)_m$ | $(R^9)_m$ |
|---|---|---|
| (1) H | (1) Ph | (1) Ph |
| (2) OH | (2) 2-Cl—Ph | (2) 2-Cl—Ph |
| (3) OMe | (3) 2-Me—Ph | (3) 2-Me—Ph |
| | (4) 2-OBu—Ph | (4) 2-OBu—Ph |
| | (5) 3-Cl—Ph | (5) 3-Cl—Ph |
| | (6) 3-Me—Ph | (6) 3-Me—Ph |
| | (7) 3-OBu—Ph | (7) 3-OBu—Ph |
| | (8) 4-Cl—Ph | (8) 4-Cl—Ph |
| | (9) 4-Me—Ph | (9) 4-Me—Ph |
| | (10) 4-OBu—Ph | (10) 4-OBu—Ph |
| | (11) 2,4-diCl—Ph | (11) 2,4-diCl—Ph |
| | (12) 3,4-diCl—Ph | (12) 3,4-diCl—Ph |
| | (13) 2,4,6-triCl—Ph | (13) 2,4,6-triCl—Ph |
| | (14) 2,4-diOBu—Ph | (14) 2,4-diOBu—Ph |
| | (15) 3,4-diOBu—Ph | (15) 3,4-diOBu—Ph |
| | (16) 3-Me-4-Cl—Ph | (16) 3-Me-4-Cl—Ph |
| | (17) 3-Cl-5-OBu—Ph | (17) 3-Cl-5-OBu—Ph |

TABLE 5

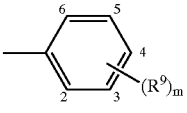
(I-5)

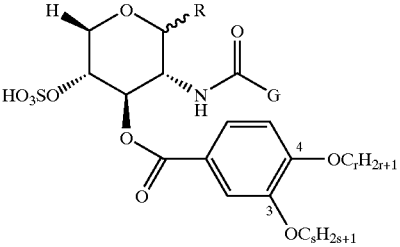

| R | G | |
|---|---|---|
| (1) H | (1) 3,4-diOC$_6$H$_{13}$—Ph | (1) 3,4-diOC$_6$H$_{13}$—Ph |
| (2) OH | (2) 3,4-diOC$_7$H$_{15}$—Ph | (2) 3,4-diOC$_7$H$_{15}$—Ph |
| (3) OMe | (3) 3,4-diOC$_8$H$_{17}$—Ph | (3) 3,4-diOC$_8$H$_{17}$—Ph |
| | (4) 3,4-diOC$_9$H$_{19}$—Ph | (4) 3,4-diOC$_9$H$_{19}$—Ph |
| | (5) 3,4-diOC$_{10}$H$_{21}$—Ph | (5) 3,4-diOC$_{10}$H$_{21}$—Ph |
| | (6) 3,4-diOC$_{11}$H$_{23}$—Ph | (6) 3,4-diOC$_{11}$H$_{23}$—Ph |
| | (7) 3,4-diOC$_{12}$H$_{25}$—Ph | (7) 3,4-diOC$_{12}$H$_{25}$—Ph |
| | (8) C$_{13}$H$_{27}$ | |

TABLE 6

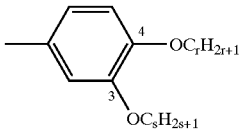
(I-6)

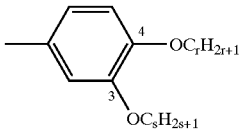

| R | G | |
|---|---|---|
| (1) H | (1) 3,4-diOC$_6$H$_{13}$—Ph | (1) 3,4-diOC$_6$H$_{13}$—Ph |
| (2) OH | (2) 3,4-diOC$_7$H$_{15}$—Ph | (2) 3,4-diOC$_7$H$_{15}$—Ph |
| (3) OMe | (3) 3,4-diOC$_8$H$_{17}$—Ph | (3) 3,4-diOC$_8$H$_{17}$—Ph |
| | (4) 3,4-diOC$_9$H$_{19}$—Ph | (4) 3,4-diOC$_9$H$_{19}$—Ph |
| | (5) 3,4-diOC$_{10}$H$_{21}$—Ph | (5) 3,4-diOC$_{10}$H$_{21}$—Ph |
| | (6) 3,4-diOC$_{11}$H$_{23}$—Ph | (6) 3,4-diOC$_{11}$H$_{23}$—Ph |
| | (7) 3,4-diOC$_{12}$H$_{25}$—Ph | (7) 3,4-diOC$_{12}$H$_{25}$—Ph |
| | (8) C$_{13}$H$_{27}$ | |

TABLE 7

(I-7)

[Chemical structure: pyranose ring with H₃C, HO₃SO, O-R, NH-C(=O)-G substituents; G includes benzoate with OC_rH_{2r+1} and OC_sH_{2s+1} groups at 3,4-positions, and a phenyl group with OC_rH_{2r+1} and OC_sH_{2s+1} at 3,4-positions]

| R | G | |
|---|---|---|
| (1) H | (1) 3,4-diOC$_6$H$_{13}$—Ph | (1) 3,4-diOC$_6$H$_{13}$—Ph |
| (2) OH | (2) 3,4-diOC$_7$H$_{15}$—Ph | (2) 3,4-diOC$_7$H$_{15}$—Ph |
| (3) OMe | (3) 3,4-diOC$_8$H$_{17}$—Ph | (3) 3,4-diOC$_8$H$_{17}$—Ph |
| | (4) 3,4-diOC$_9$H$_{19}$—Ph | (4) 3,4-diOC$_9$H$_{19}$—Ph |
| | (5) 3,4-diOC$_{10}$H$_{21}$—Ph | (5) 3,4-diOC$_{10}$H$_{21}$—Ph |
| | (6) 3,4-diOC$_{11}$H$_{23}$—Ph | (6) 3,4-diOC$_{11}$H$_{23}$—Ph |
| | (7) 3,4-diOC$_{12}$H$_{25}$—Ph | (7) 3,4-diOC$_{12}$H$_{25}$—Ph |
| | (8) C$_{13}$H$_{27}$ | |

TABLE 8

(I-8)

[Chemical structure: pyranose ring with HO₃SO, HO₃SO, O-R, NH-C(=O)-G substituents; G includes benzoate with OC_rH_{2r+1} and OC_sH_{2s+1} groups at 3,4-positions, and a phenyl group with OC_rH_{2r+1} and OC_sH_{2s+1} at 3,4-positions]

| R | G | |
|---|---|---|
| (1) H | (1) 3,4-diOC$_6$H$_{13}$—Ph | (1) 3,4-diOC$_6$H$_{13}$—Ph |
| (2) OH | (2) 3,4-diOC$_7$H$_{15}$—Ph | (2) 3,4-diOC$_7$H$_{15}$—Ph |
| (3) OMe | (3) 3,4-diOC$_8$H$_{17}$—Ph | (3) 3,4-diOC$_8$H$_{17}$—Ph |
| | (4) 3,4-diOC$_9$H$_{19}$—Ph | (4) 3,4-diOC$_9$H$_{19}$—Ph |
| | (5) 3,4-diOC$_{10}$H$_{21}$—Ph | (5) 3,4-diOC$_{10}$H$_{21}$—Ph |
| | (6) 3,4-diOC$_{11}$H$_{23}$—Ph | (6) 3,4-diOC$_{11}$H$_{23}$—Ph |
| | (7) 3,4-diOC$_{12}$H$_{25}$—Ph | (7) 3,4-diOC$_{12}$H$_{25}$—Ph |
| | (8) C$_{13}$H$_{27}$ | |

Salts

The compounds of formulae (I) of the present invention may be converted into the corresponding salts by conventional means. Non-toxic and water-soluble salts are preferred. Suitable salts, for example, include: salts of alkali metals (e.g. sodium, potassium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, lysine, arginine, N-methyl-D-glucamine, tris(hydroxymethyl)methyl-amine).

The compounds of formulae (I) and salts thereof may be converted into the corresponding hydrates by conventional means.

Process for the Preparation

The compounds of the present invention of the formula (I), may be prepared by methods described in Japanese Kokoku-koho Hei 4-74359 (EP 0226381) or Japanese Kokai-koho Hei 1-52793 (EP 0288888), a similar methods thereof or a conventional means.

Besides, the preparation of sodium salt of the compound of the present invention of the formula (I-A) is described in detail as example 2, 3, 5 and 6 in Japanese Kokai-koho Hei 6-41175 (EP 0226381) and tris(hydroxymethyl)methyl ammonium salt thereof as example 4.

The compounds of formulae (I) of the present invention may be converted into the various salts by the above methods or a conventional means.

Toxicity

The toxicity of the compounds of the present invention of the formula (I) is very low and therefore, the compounds may be considered safe for pharmaceutical use. For example, LD$_{50}$ of 2-deoxy-2-[3S-(9-phenylnonanoyloxy) tetradecanoyl]-amino-3-O-(9-phenylnonanoyl)-4-O-sulfo-D-glucopyranose sodium salt (The compound (1) described hereinafter) is 60–70 mg/kg on SD rats were administrated by intravenous injection.

Technical Filed

Application for Pharmaceuticals

The compound of the present invention of the formula (I) is useful for prevention and/or treatment of diseases, for example, diseases induced by an abnormal acceleration of immunological function, for example, allergic diseases, e.g. allergic asthma, atopic dermatitis containing urticaria, allergic rhinitis, allergic conjunctivitis, allergic bronchopulmonary aspergillosis, allergic eosinophilic gastroenteritis, hyper IgE syndrome containing pyogenic dermatitis, low of leukocyte wandering, and atopic dermatitis; PIE syndrome, pulmonary eosinophilia, e.g. Loeffler syndrome, chronic eosinophilic pneumonia, acute eosinophilic pneumonia, tropical eosinophilia, allergic granulomatous angiitis, allergic bronchopulmonary mycosis, eosinophilia; eosinophilic fasciitis and autoimmune diseases, e.g. chronic rheumatism, psoriasis, multiple sclerosis and ulcerative colitis in animal including human beings, especially human beings.

For the purpose above described, the compounds of formulae (I) of the present invention, non-toxic salts or hydrates may be normally by administered systemically or locally usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders, and granules.

Capsules include hard capsules and soft capsules.

In such compositions, one or more of the active compound(s) may be admixed with at least one inert diluent (such as lactose, mannitol, glucose, hydroxypropyl cellulose, microcrystalline cellulose, starch, polyvinylpyrrolidone or magnesium metasilicate aluminate). The compositions may also comprise, as is normal practice, additional substances other than inert diluent: e.g. lubricating agents (such as magnesium stearate), disintegrating agents (such as cellulose calcium glycolate), stabilizing agents, and agents to assist dissolution (such as glutamic acid or aspartic acid).

The tablets or pills may, if desired, be coated with a film of gastric or enteric material (such as sugar, gelatin, hydroxypropyl cellulose or hydroxypropylmethyl cellulose phthalate), or be coated with two or more films. And further, coating may include containment within capsules of absorbable materials such as gelatin.

Liquid compositions for oral administration include pharmaceutically acceptable emulsions, solutions, syrups and elixirs. In such compositions, one or more of the active compound(s) may be contained in an inert diluent(s) commonly used in the art (e.g. purified water or ethanol). Besides inert diluent, such compositions may also comprise adjuvants (such as wetting agents or suspending agents), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (such as sodium sulfate), isotonic buffer (such as sodium chloride, sodium citrate or citric acid). For preparation of such spray compositions, for example, the method described in the U.S. Pat. No. 2,868,691 or 3,095,355 may be used.

Injections for parenteral administration include sterile aqueous or non-aqueous solutions, suspensions and emulsions. Aqueous solutions and suspensions may include distilled water for injection or physiological salt solution. Non-aqueous solutions and suspensions may include propylene glycol, polyethylene glycol, vegetable oil such as olive oil, alcohol such as ethanol or POLYSORBATE80 (registered trade mark).

Injections may comprise additional ingredients other than inert diluent: e.g. preserving agents, wetting agents, emulsifying agents, dispersing agents, stabilizing agents, assisting agents such as agents to assist dissolution (e.g. glutamic acid or aspartic acid).

They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile diluent(s) for injection immediately before use.

Other compositions for parenteral administration include liquids for external use, and endermic liniments, ointment, suppositories for rectal administration and pessaries for vaginal administration which comprise one or more of the active compound(s) and may be prepared by methods known per se.

Best Mode for Carrying Out Invention

The following examples are illustrated the present invention, but not limit the present invention.

The following compounds are used in examples.

Compound (1)

2-deoxy-2-[3S-(9-phenylnonanoyloxy)tetradecanoyl] amino-3-O-(9-phenylnonanoyl)-4-O-sulfo-D-glucopyranose sodium;

It is prepared by method described in example 2, 3, 5 or 6 in Japanese Kokai-koho Hei 6-41175 (EP 0226381).

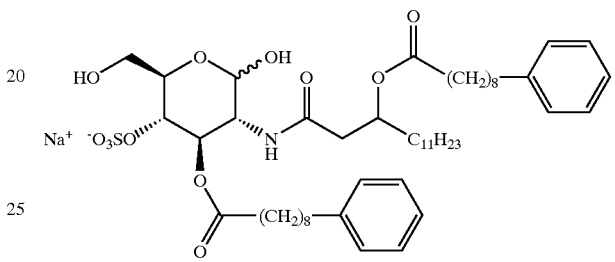

(1)

The abbreviation in examples means as follows.

DNFB: 2,4-dinitrofluorobenzene,
DNP: 2,4-dinitrophenol,
BALF: bronchoalveolar lavage fluid,
OVA: ovalbumin,
PCA: passive cutaneous anaphylaxis.

EXAMPLE 1

Effect on DNFB-induced Mouse Ear Edema (Oral)

[Method]

Anti-DNP-IgE antibody (3 μg/body) was administered from the caudal vein of each of female Balb/c mice of 7 weeks of age, and the reaction was induced by applying 25 μl of a 0.15% DNFB-containing acetone:olive oil (3:1) mixed solution (hereinafter referred to as "antigen") to each of both sides of the left and right auricles 24 hours after the administration. Each compound to be tested was administered orally or intravenously 1 hour before the reaction induction. Before the reaction induction and 1 hour after the reaction induction, auricle thickness was measured using a dial sickness gage, and the average value of the left and right auricle thicknesses was used as the measured value at respective time. The value was shown by the increasing ratio of the auricle thickness from before the reaction induction. The results are shown in Table 9. In Table 9, treatments in each group are as follows.

Vehicle: anti-DNP-IgE antibody administration+vehicle application+vehicle administration Control: anti-DNP-IgE antibody administration+antigen application+vehicle administration Compound (1): anti-DNP-IgE antibody administration+ antigen application+Compound (1) administration

TABLE 9

Inhibition effect on DNFB-induced mouse ear edema

| Compound tested | Increasing ratio of auricle thickness (%) |
|---|---|
| Vehicle | 6.2 ± 1.2 |
| Control | 18.7 ± 3.0** |
| Compound (1) 10 mg/kg p.o. | 14.3 ± 1.8 |
| Compound (1) 40 mg/kg p.o. | 10.2 ± 1.6* |
| Compound (1) 10 mg/kg i.v. | 16.4 ± 1.9 |

*: Significant difference of $p < 0.05$ (Student's t-test) against the control group.
**: Significant difference of $p < 0.01$ (Dunnett's t-test) against the vehicle group.

In the control group, 18.7% increase in the auricle thickness was observed 1 hour after the antigen application, when compared with the value before the reaction. On the other hand, in Compound (1), increase in the auricle thickness, for example by oral administration of 40 mg/kg, was only 10.2%, and, as a result, it inhibited 45% of increase in the auricle thickness.

EXAMPLE 2

Effectiveness on IgE Antibody Production and IL-5 Production and Eosinophils Infiltration in BALF, Using a Mouse Allergic Airway Inflammation Model

[Method]

The test was carried out in accordance with the method of Nagai et al. (see H. Nagai, H. Takeda, S. Yamaguchi, H. Tanaka, A. Matsuo and N. Inagaki, "The effect of thromboxane $A_2$ receptor antagonist BAY-u-3405 on experimental allergic reactions", *Prostaglandins*, 50, 75–87, 1995). Specifically, 0.5 ml of physiological saline containing 50 μg of OVA and 1 mg of aluminum hydroxide gel as adjuvant was injected twice at 12 day interval into the abdominal cavity of each of male Balb/c mice of 7 weeks of age for active sensitization. After 22, 26 and 30 days of the initial sensitization, each animal was forced to inhale 1% OVA solution for 30 minutes using an ultrasonic nebulizer to prepare a mouse allergic airway inflammation model. Total blood and BALF were collected 8 hours after the final antigen inhalation. The collected blood was allowed to stand overnight at room temperature, and then centrifuged at 300 rpm for 15 minutes, and the light yellow transparent fraction separated into the supernatant was used as an antiserum. The IgE antibody titer in the antiserum was measured by 24 hours' heterogeneous (rat) PCA. On the other hand, the collected BALF supernatant was used as a sample for cytokine measurement, and the cell pellets after preparation were counted as an index of the infiltration of inflammatory cells. Each compound to be tested was continuously administered 5 days starting from the day before each sensitization and 10 days starting from the day before inhalation, at a dose of 10, 30 or 100 mg/kg in the case of oral administration or 10 mg/kg in the case of intraperitoneal or intravenous injection. Results of the measurement of IgE antibody titer in serum and amount of IL-5 and the number of eosinophils in BALF are shown in Tables 10, 11 and 12, respectively. The treatments in each group shown in each table are as follows.

Physiological saline: physiological saline stimulation+vehicle administration
Control: OVA stimulation+vehicle administration
Compound (1): OVA stimulation+Compound (1) administration

TABLE 10

Serum IgE antibody production inhibition effect in mouse allergic airway inflammation model

| Compound tested | Serum IgE antibody titer |
|---|---|
| Physiological saline | 8.0 ± 0.0 |
| Control | 460.8 ± 45.8***[a] |
| Compound (1) 10 mg/kg p.o. | 304.0 ± 68.2 |
| Compound (1) 30 mg/kg p.o. | 176.0 ± 35.2** |
| Compound (1) 100 mg/kg p.o. | 120.0 ± 30.1** |
| Compound (1) 10 mg/kg i.p. | 69.3 ± 17.6***[b] |
| Compound (1) 10 mg/kg i.v. | 20.0 ± 3.7***[b] |

**: Significant difference of $p < 0.01$ (Dunnett's t-test) against the control group.
***[a]: Significant difference of $p < 0.0001$ (Student's t-test) against the physiological saline group.
***[b]: Significant difference of $p < 0.0001$ (Student's t-test) against the control group.

TABLE 11

BALF IL-5 production inhibition effect in mouse allergic airway inflammation model

| Compound tested | Amount of IL-5 in BALF (pg/BALF) |
|---|---|
| Physiological saline | 5.0 ± 0.0 |
| Control | 118.5 ± 29.0**[a] |
| Compound (1) 10 mg/kg p.o. | 65.1 ± 15.9 |
| Compound (1) 30 mg/kg p.o. | 50.8 ± 13.7 |
| Compound (1) 100 mg/kg p.o. | 26.7 ± 7.5** |
| Compound (1) 10 mg/kg i.p. | 9.2 ± 1.5**[b] |
| Compound (1) 10 mg/kg i.v. | 16.2 ± 3.8**[b] |

**: Significant difference of $p < 0.01$ (Dunnett's t-test) against the control group.
**[a]: Significant difference of $p < 0.01$ (Student's t-test) against the physiological saline group.
**[b]: Significant difference of $p < 0.01$ (Student's t-test) against the control group.

TABLE 12

BALF eosinophils infiltration inhibition effect in mouse allergic airway inflammation model

| Compound tested | The number of eosinophils in BALF (× $10^5$ cells/BALF) |
|---|---|
| Physiological saline | 0.0 ± 0.0 |
| Control | 3.9 ± 1.4*[a] |
| Compound (1) 10 mg/kg p.o | 1.4 ± 0.4* |
| Compound (1) 30 mg/kg p.o. | 0.7 ± 0.2** |
| Compound (1) 100 mg/kg p.o. | 0.3 ± 0.1** |
| Compound (1) 10 mg/kg i.p. | 0.0 ± 0.0*[b] |
| Compound (1) 10 mg/kg i.v. | 0.1 ± 0.0*[b] |

*[a]: Significant difference of $p < 0.05$ (Student's t-test) against the physiological saline group.
*[b]: Significant difference of $p < 0.05$ (Student's t-test) against the control group.
*, **: Significant difference of $p < 0.05, 0.01$ (Dunnett's t-test) against the control group.

EXAMPLE 3

Effect on Mouse Compound 48/80-induced Itch Model

[Method]

This test was carried out in accordance with the method of Kubo et al. (Michinori Kubo, Hideaki Matsuda, Takeshi Itadaki, Yasuko Ido and Masayuki Yoshikawa, Studies on herb medicine and jifushi (first report), Anti-itching activity of 70% ethanol extract of jifushi and screening of effective component, *Journal of the Pharmaceutical Society of Japan*, 117(4), 193–201, 1997). Specifically, 0.1 ml of physiological saline containing Compound 48/80 (manufactured by Sigma Chemical Company) (100 µg) was administered subcutaneously into the dorsal part of each male ddy mouse of 6 to 7 weeks of age to induce scratching behavior. The scratching behavior was judged by measuring the number of times of scratching for 20 minutes immediately after the injection, by setting the behavior of each mouse to scratch the injected part with a hind leg for 1 second or more as one. Each compound to be tested was administered intravenously 1 hour before the induction. The results are shown in Table 13.

TABLE 13

Effect on mouse Compound 48/80-induced itch model

| Compound tested | The number of times of scratching |
|---|---|
| Physiological saline | 2.9 ± 1.5 |
| Control | 82.9 ± 17.3 |
| Compound (1) 1 mg/kg | 68.6 ± 18.8 |
| Compound (1) 3 mg/kg | 61.3 ± 9.9 |
| Compound (1) 10 mg/kg | 26.8 ± 16.8* |
| Compound (1) 30 mg/kg | 6.3 ± 4.4** |

*, **: Significant difference of $p < 0.05, 0.01$ (Dunnett's t-test) against the control group.

Compound (1) significantly reduced scratching behavior of the mouse itch-induced with Compound 48/80 by 10 or 30 mg/kg of intravenously administration.

EXAMPLE 4

Inhibition on the in vitro OVA-stimulated Cytokine Production by Spleen Cells Isolated from OVA-sensitized Mice

[Method]

OVA-sensitized animals were prepared in accordance with the method of Nagai et al. (the method described in Example 2). Specifically, 0.5 ml of physiological saline containing 50 µg of OVA and 1 mg of aluminum hydroxide gel as adjuvant was injected twice at 12 day interval into the abdominal cavity of each of male Balb/c mice of 7 weeks of age for active sensitization. After 22, 26 and 30 days of the initial sensitization, each animal was forced to inhale 1% OVA solution for 30 minutes using an ultrasonic nebulizer. After 8 hours of the final antigen inhalation, the spleen was collected to prepare spleen cells. The spleen cells were cultured for 96 hours in the presence of 1 mg/ml of OVA, and the cytokine released in the culture supernatant was determined by ELISA method. Each of the compounds to be tested was added to a final concentration of 0.3, 1, 3, 10 or 30 µM simultaneously with OVA. Results of the measurement of IL-2, IFN-γ and IL-4 are respectively shown in Tables 14, 15 and 16.

TABLE 14

OVA-stimulated IL-2 production inhibition effect

| Compound tested | Amount of IL-2 (pg/ml) |
|---|---|
| Control | 145.9 ± 14.9 |
| Compound (1) 0.3 µM | 48.4 ± 3.0** |
| Compound (1) 1 µM | 36.1 ± 5.0** |
| Compound (1) 3 µM | 22.9 ± 2.9** |
| Compound (1) 10 µM | 11.7 ± 2.2** |

TABLE 14-continued

OVA-stimulated IL-2 production inhibition effect

| Compound tested | Amount of IL-2 (pg/ml) |
|---|---|
| Control | 145.9 ± 14.9 |
| Compound (1) 30 µM | 4.3 ± 1.7** |

**: Significant difference of $p < 0.01$ (Dunnett's t-test) against the control group.

TABLE 15

OVA-stimulated IFN-γ production inhibition effect

| Compound tested | Amount of IL-2 (pg/ml) |
|---|---|
| Control | 2460.3 ± 305.0 |
| Compound (1) 0.3 µM | 1462.9 ± 202.8** |
| Compound (1) 1 µM | 658.1 ± 66.6** |
| Compound (1) 3 µM | 457.6 ± 51.0** |
| Compound (1) 10 µM | 349.7 ± 81.0** |
| Compound (1) 30 µM | 160.5 ± 42.9** |

**: Significant difference of $p < 0.01$ (Dunnett's t-test) against the control group.

TABLE 16

OVA-stimulated IL-4 production inhibition effect

| Compound tested | Amount of IL-2 (pg/ml) |
|---|---|
| Control | 335.9 ± 42.5 |
| Compound (1) 0.3 µM | 253.0 ± 45.9 |
| Compound (1) 1 µM | 203.3 ± 37.3 |
| Compound (1) 3 µM | 139.0 ± 19.3** |
| Compound (1) 10 µM | 67.9 ± 8.1** |
| Compound (1) 30 µM | 12.8 ± 1.1** |

**: Significant difference of $p < 0.01$ (Dunnett's t-test) against the control group.

Compound (1) significantly inhibited in vitro OVA-stimulated IL-2 production and IFN-γ production by spleen cells isolated from OVA-sensitized mice with 0.3 to 30 µM and the IL-4 production with 3 to 30 µM.

Formulation Example

Formulation Example 1

The following components were admixed in conventional method. The solution was sterilized in conventional manner, placed 1 ml portions into ampoules and freeze-dried to obtain 100 ampoules each containing 50 mg of the active ingredient.

2-deoxy-2-[3S-(9-phenylnonanoyloxy)tetradecanoyl]
  amino-3-O-(9-phenylnonanoyl)-4-O-sulfo-D-
  glucopyranose sodium (Compound 1) . . . 5.00 g
55% ethanol . . . 100 ml Formulation Example 2

The following components were admixed in conventional method and punched out to obtain 100 tablets each containing 5 mg of active ingredient.

2-deoxy-2-[3S-(9-phenylnonanoyloxy)tetradecanoyl]
  amino-3-O-(9-phenylnonanoyl)-4-O-sulfo-D-
  glucopyranose sodium (compound 1) . . . 500 mg
Carboxymethyl Cellulose calcium . . . 200 mg
Magnesium stearate . . . 100 mg
Microcrystalline cellulose . . . 9.2 g

What is claimed is:

1. A method of suppressing an immune response comprising administering to a patient in need of treatment an effective amount of a glucopyranose compound of the formula (I):

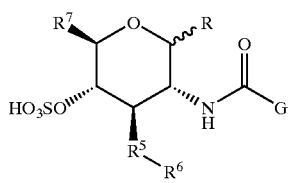

wherein R is hydrogen, hydroxy or C1–4 alkoxy,

G is (1)

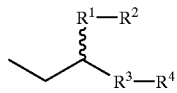

in which $R^1$ is a single bond or C2–20 oxycarbonylalkyl, $R^2$ is hydrogen or

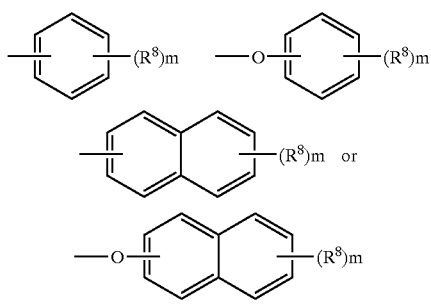

in which $R^8$ is hydrogen, C1–7 alkyl, C1–7 alkoxy or a halogen atom, m is 1, 2, or 3;

$R^3$ is C1–20 alkylene, $R^4$ is hydrogen or

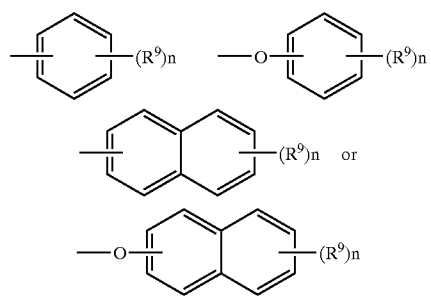

in which $R^9$ is hydrogen, C1–7 alkyl, C1–7 alkoxy or a halogen atom, n is 1, 2, or 3; or (2)

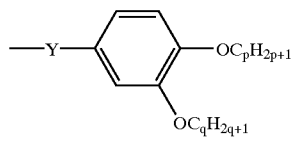

in which Y is a single bond or C1–4 alkylene, and p and q are each independently an integer of from 6–12;

$R^5$ is C2–20 oxycarbonylalkyl, $R^6$ is hydrogen or

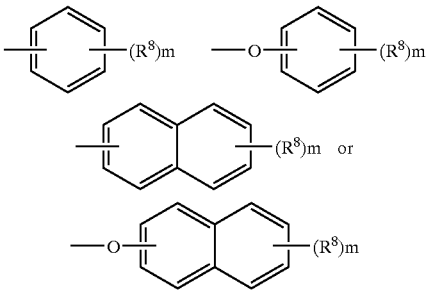

in which $R^8$ and m are as hereinbefore defined; or $R^5$—$R^6$ is

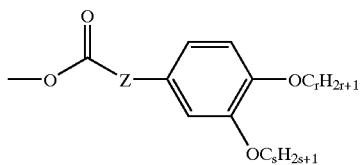

in which Z is a single bond or C1–4 alkylene, and r and s are each independently an integer of from 6–12;

$R^7$ is hydrogen, methyl, hydroxymethyl or sulfoxymethyl;

with the proviso that (1) $R^2$, $R^4$ and $R^6$ are not hydrogen at the same time, (2) when $R^1$ is C2–20 oxycarbonylalkyl, then $R^2$ bonds to alkyl in $R^1$, (3) when $R^5$ is C2–20 oxycarbonylalkyl, then $R^6$ bonds to alkyl in $R^5$;

or a non-toxic salt thereof.

2. The method according to claim 1, wherein the glucopyranose compound is 2-deoxy-2-[3S-(9-phenylnonanoyloxy)tetradecanoyl]amino-3-O-(9-phenylnonanoyl)-4-O-sulfo-D-glucopyranose.

3. A method of treating, an allergic disease, said method comprising administering to a patient a pharmaceutically effective amount of a glucopyranose compound of formula (I) of claim 1, or non-toxic salts thereof, as an active ingredient, and a pharmaceutically acceptable carrier or diluent.

4. A method of treating, an autoimmune disease, said method comprising administering to a patient a pharmaceutically effective amount of a glucopyranose compound of formula (I) of claim 1, or non-toxic salts thereof, as an active ingredient, and a pharmaceutically acceptable carrier or diluent.

5. A method of inhibiting IgE production, said method comprising administering to a patient a pharmaceutically effective amount of a glucopyranose compound of formula (I) of claim 1, or non-toxic salts thereof, as an active ingredient, and a pharmaceutically acceptable carrier or diluent.

6. A method of inhibiting interleukin 5 production, said method comprising administering to a patient a pharmaceutically effective amount of a glucopyranose compound of formula (I) of claim 1, or non-toxic salts thereof, as an active ingredient, and a pharmaceutically acceptable carrier or diluent.

7. A method of inhibiting eosinophil infiltration, said method comprising administering to a patient a pharmaceutically effective amount of a glucopyranose compound of formula (I) of claim 1, or non-toxic salts thereof, as an active ingredient, and a pharmaceutically acceptable carrier or diluent.

8. A method of inhibiting interleukin 4 production, said method comprising administering to a patient a pharmaceutically effective amount of a glucopyranose compound of formula (I) of claim 1, or non-toxic salts thereof, as an active ingredient, and a pharmaceutically acceptable carrier or diluent.

9. A method of inhibiting interleukin 2 production, said method comprising administering to a patient a pharmaceutically effective amount of a glucopyranose compound of formula (I) of claim 1, or non-toxic salts thereof, as an active ingredient, and a pharmaceutically acceptable carrier or diluent.

10. A method of inhibiting interleukin $\gamma$ production, said method comprising administering to a patient a pharmaceutically effective amount of a glucopyranose compound of formula (I) of claim 1, or non-toxic salts thereof, as an active ingredient, and a pharmaceutically acceptable carrier or diluent.

* * * * *